United States Patent [19]
Raylman et al.

[11] Patent Number: 5,932,879
[45] Date of Patent: Aug. 3, 1999

[54] SOLID STATE BETA-SENSITIVE SURGICAL PROBE

[75] Inventors: Raymond R. Raylman, Morgantown, W. Va.; Richard L. Wahl, Ann Arbor, Mich.

[73] Assignee: Regents of the University of Michigan, Ann Arbor, Mich.

[21] Appl. No.: 08/851,360

[22] Filed: May 5, 1997

Related U.S. Application Data

[63] Continuation-in-part of application No. 08/643,913, May 7, 1996, Pat. No. 5,744,805.

[51] Int. Cl.$^6$ .................................................. G01T 1/161
[52] U.S. Cl. .................................... 250/370.06; 250/367
[58] Field of Search ................................ 250/367, 370.06

[56] References Cited

U.S. PATENT DOCUMENTS

| 3,670,719 | 6/1972 | Kobayashi et al. ................. 600/436 |
| 4,677,982 | 7/1987 | LLinas et al. ........................ 600/473 |

FOREIGN PATENT DOCUMENTS

| 0 079 079 | 5/1983 | European Pat. Off. .......... 250/370.06 |
| 60-188869 | 9/1985 | Japan ................................... 250/367 |

OTHER PUBLICATIONS

S. Peterström and G. Holmes, "Semiconductor Counters for Nuclear Radiations Produced by Ion Implantation." Nuclear Instruments and Methods, vol. 119, No. 1, pp. 151–155, Jul. 1974.

*Primary Examiner*—Constantine Hannaher
*Attorney, Agent, or Firm*—Medlen & Carroll, LLP

[57] ABSTRACT

An intraoperative system made be used for preferentially detecting beta radiation over gamma radiation emitted from a radiopharmaceutical. The system has ion-implanted silicon charged-particle detectors for generating signals in response to received beta particles. A preamplifier may be located in proximity to the detector filters and amplifies the signal. Also, a wire may be used to couple the probe to a processing unit for amplifying and filtering the signal.

23 Claims, 13 Drawing Sheets

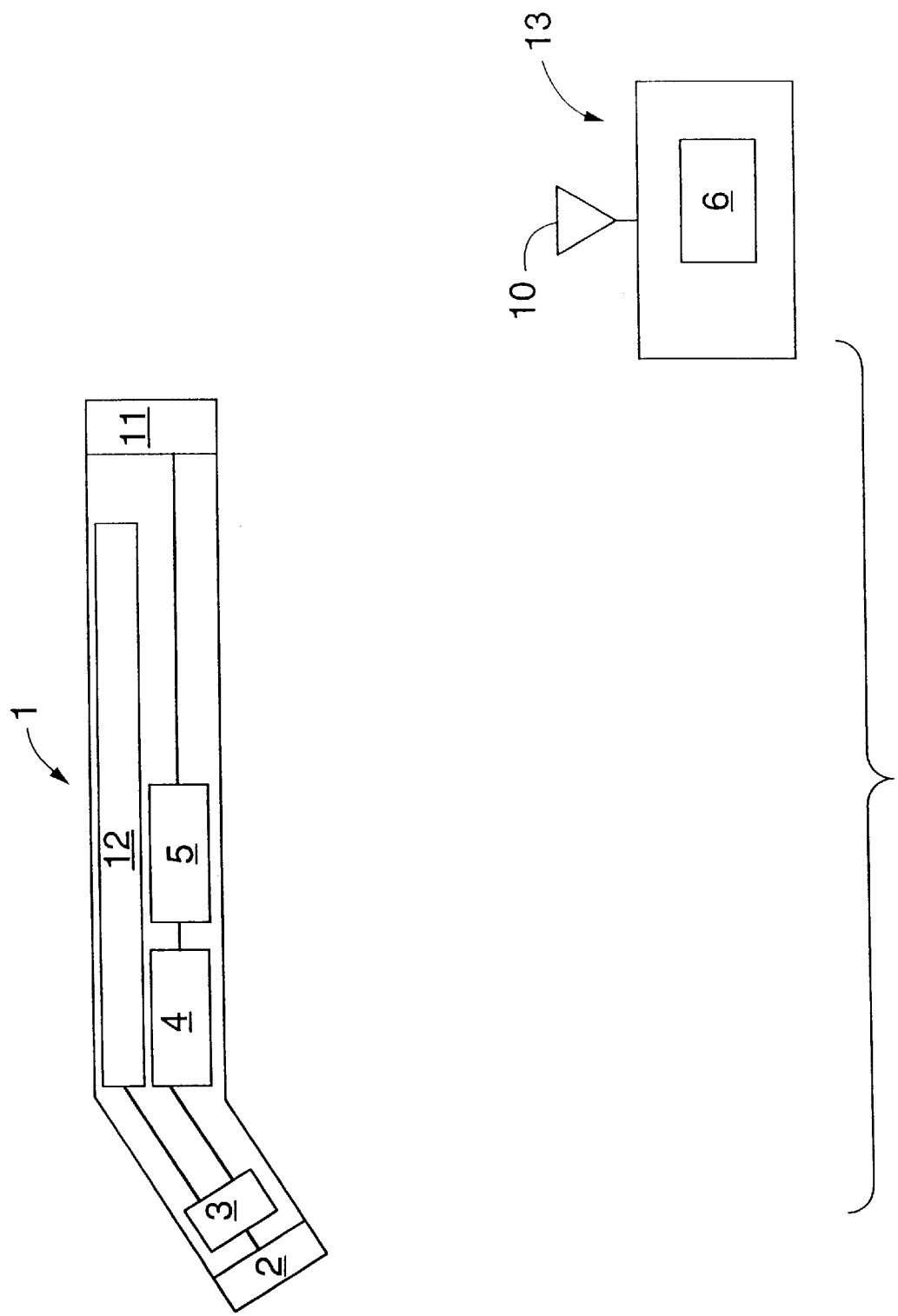

SOLID STATE BETA-SENSITIVE SURGICAL PROBE

This application is a Continuation-in-part of Ser. No. 08/643,913, now U.S. Pat. No. 5,744,805, filed May 7, 1996, issued Apr. 28, 1998.

FIELD OF THE INVENTION

The present invention relates generally to the field of radiation detection probes, and more specifically to a beta-sensitive radiation probe used to detect tissue labelled with beta-emitting radiopharmaceuticals.

BACKGROUND OF THE INVENTION

The surgical excision of diseased tissue within the body, such as a tumor or abscess, is often complicated by the inability of the surgeon to visually differentiate the diseased tissue from the normal tissue. This problem is particularly acute in the field of surgical oncology, where small numbers of tumor cells can infiltrate areas of normal tissue both adjacent to and remote from the main tumor mass. Importantly, the failure to remove all of the diseased tissue during the procedure often results in a continuation or recurrence of the original problem.

One potential solution to this problem involves the detection of radiolabelled monoclonal antibodies and other radiopharmaceuticals, which are preferentially accumulated in diseased tissues such as cancer cells. Although intraoperative probes have been developed for use with several types of radioactive materials, the historical emphasis has been on the detection of gamma radiation in particular (gamma rays or photons). See Harris et al., *Nucleonics* 14:102–8 (1956); Morris et al., *Phys. Med. Biol.* 16:397–404 (1971); Woolfenden et al., *Chest* 85:84–88 (1984). Unfortunately, the prior art devices designed for use with gamma-emitting radiopharmaceuticals suffer from two significant problems: 1) the tumor-to-background ratios are non-optimal for the reliable differentiation of tumors, and 2) the detection of distant sources of gamma rays further reduces the already low tumor-to-background contrast. The longer path length of gamma radiation in body tissues creates significant background contamination from distant accumulations of the radiopharmaceutical, making the detection of nearby tagged tissues difficult or impossible.

As a result, there has been a renewed interest in developing intraoperative probes which focus primarily on the detection of beta emissions (positrons and/or electrons), particularly in light of the recent discovery of positron emitters with high affinity for cancers, such as $^{18}$F-labeled-Fluoro-2-Deoxy-D-Glucose (FDG). See Wahl et al., *Cancer* 67:1550–54 (1991). However, recent attempts to design an accurate beta-sensitive intraoperative probe have been complicated by the fact that positron-emitting radiopharmaceuticals such as $^{18}$F-FDG create two 511 keV annihilation photons when the positron subsequently collides with an electron. The detection of these highly penetrating gamma rays greatly reduces the observed tumor-to-background contrast gained by the use of these radiopharmaceuticals.

In response, several attempts have been made to design detectors to maximize the detected positron-to-photon ratio. One possible approach to limit the effect of the annihilation photon emissions relies upon energy discrimination to reduce the photon contribution to the signal. See Raylman et al., *J. Nucl. Med.* 36:1869–74 (1995). The dominant mode of interaction for the 511 keV photons produced during annihilation of the positron and electron is a Compton scattering of electrons, generally below 340 keV. In contrast, the positron interacts with the detector by producing a spectrum of energies, some of which are above the Compton edge of approximately 340 keV for annihilation photons. Accordingly, by selectively counting only those events with energies above the Compton edge, the probe becomes selectively sensitized to the electrons and positrons emitted by radiopharmaceuticals such as $^{18}$F, which create annihilation photons.

Unfortunately, most of the detectors proposed thus far for use as positron probes have utilized plastic scintillators. See Lerch et al., *Am. J Physiol.* 242:H62–H67 (1982); Raylman et al., *J. Nucl. Med.* 35:909–13 (1994); Daghighian et al., *Med. Phys.* 36:1869–74 (1995). The application of the energy discrimination technique with plastic scintillators is problematic due to the poor energy resolution of this material, which is a measure of how well the energy of a specific type of radiation (such as gamma rays) can be defined. Moreover, inefficiencies in the collection of the scintillation light produced by the plastic scintillators also reduce the energy resolution of these detection devices.

An alternative method and device proposed and patented by Daghighian et al. involves the use of two separate plastic scintillation detectors, whereby the signals from the shielded outer detector are used to correct for photon contamination of the signal from the inner detector. See Daghighian et al., *Med. Phys.* 21:153–7 (1994); U.S. Pat. No. 5,008,546 to Mazziotta et al. Correction of signal contamination is accomplished by a weighted subtraction of the outer detector count rate from the inner detector count rate. The weighting factor is the ratio of the gamma counting efficiencies of the two detectors, which is calculated during a relatively simple calibration procedure.

While the use of a second detector to measure the background contamination is somewhat effective, this addition unfortunately results in a probe tip which is always physically larger than a single detector. Therefore, the practical application of this type of probe is problematic where space is a premium, such as with intraluminal probes and other situations where the surgical field is small. Moreover, the reduction of the surgical field continues to increase as minimally invasive surgical procedures are developed, and therefore a useful alternative to the two-detector method is needed. Furthermore, it is not clear that the background subtraction/weighting function remains constant when the probe is presented with gamma rays entering the detector volume other than through the front window. This problem is very often present in many common surgical applications.

Accordingly, there is still a substantial need in the art for an intraoperative probe which can differentiate diseased tissue based on beta emissions from a radiopharmaceutical. The probe must also have a minimal size for less intrusive operation during surgery, while at the same time provide increased sensitivity and selectivity.

SUMMARY OF THE INVENTION

The present invention contemplates a method for detecting radiopharmaceuticals within diseased tissue. In one embodiment, the method comprises the steps of a) providing: i) a patient having a region of diseased tissue, ii) a radiopharmaceutical capable of emitting beta particles and gamma radiation, and iii) an ion-implanted silicon detector; b) administering said radiopharmaceutical to said patient; and c) using said ion-implanted silicon detector to preferentially detect beta particles emitted from said radiopharmaceutical within said region over gamma radiation.

In one preferred embodiment, the step of discriminating a component of an electrical signal produced by said detector when struck by said beta particles and said gamma radiation. Said component of said electrical signal may be produced by said detector when struck by said gamma radiation.

While it is not intended that the present invention be limited by the particular radiopharmaceutical, a preferred pharmaceutical is $^{18}$F-labeled-Fluoro-2-Deoxy-D-Glucose.

The present invention also contemplates a probe system comprising a probe having an ion-implanted silicon detector, whereby beta particles emitted from a radiopharmaceutical within a diseased tissue are preferentially detected over gamma radiation. In one embodiment, the means for discriminating comprises stacked detectors.

In another preferred embodiment, said probe further comprises a means for discriminating a component of an electrical signal produced by said detector when struck by said beta particles and said gamma radiation, said means for discriminating coupled to said detector.

In another preferred embodiment, said component of said electrical signal is produced by said detector when struck by said gamma radiation.

In another preferred embodiment, said probe further comprises a) a preamplifier for amplifying said electrical signal, said preamplifier coupled to said detector; and b) an amplifier for further amplifying said electrical signal, said amplifier coupled between said preamplifier and said means for discriminating.

In another preferred embodiment, the probe system further comprises a counter for counting the number of received beta particles, said counter coupled to said means for discriminating.

In another preferred embodiment, the probe system further comprises a) a transmitter for transmitting said electrical signal as a transmitted signal, said transmitter coupled to said means for discriminating; and b) a receiver for receiving said transmitted signal, said receiver coupled to said counter.

In another embodiment, said probe further comprises a battery.

In another preferred embodiment, said transmitter is an optical transmitter, said receiver is an optical receiver and said transmitted signal is an optical signal. In an alternative embodiment, said optical transmitter is an infrared transmitter, said optical receiver is an infrared receiver and said optical signal is an infrared signal. In an alternative embodiment, said transmitter is a radio transmitter, said receiver is a radio receiver and said transmitted signal is a radio signal.

The present invention also contemplates a probe system for detecting radiation emitted from a radiopharmaceutical in a diseased tissue, comprising a) a probe having a radiation detector which generates an electrical signal in response to the passage of radiation into said detector from the radiopharmaceutical in the diseased tissue; and b) an optical transmitter coupled to said probe for transmitting said electrical signal as an optical signal to a remote location. Alternatively, the present invention contemplates a probe system for detecting radiation emitted from a radiopharmaceutical in a diseased tissue, comprising: a) a probe having a first radiation detector which generates an electrical signal in response to the passage of radiation into said first detector from a radiopharmaceutical in diseased tissue; and b) an optical transmitter coupled to said probe for transmitting said electrical signal as an optical signal to a remote location. In a preferred embodiment, the system further comprises a second radiation detector, said first detector capable of detecting beta particles and gamma radiation and serving to shield said second detector from at least a portion of the beta particles detected by said first detector.

The present invention also contemplates a probe comprising an ion-implanted silicon detector, whereby beta particles emitted from a radiopharmaceutical within a diseased tissue are preferentially detected over gamma radiation.

In another preferred embodiment, the probe further comprises a means for discriminating a component of an electrical signal produced by said detector when struck by said beta particles and said gamma radiation, said means for discriminating coupled to said detector.

In another preferred embodiment, said component of said electrical signal is produced by said detector when struck by said gamma radiation.

In another preferred embodiment, the probe further comprises a) a preamplifier for amplifying said electrical signal, said preamplifier coupled to said detector; and b) an amplifier for further amplifying said electrical signal, said amplifier coupled between said preamplifier and said means for discriminating.

In another preferred embodiment, the probe further comprises a counter for counting the number of received beta particles, said counter coupled between said amplifier and said means for discriminating.

The present invention is not limited by the number of detectors utilized. While the present invention contemplates any number of detectors, in another embodiment, the present invention contemplates a device comprising: a) a housing, comprising a rear portion and a front portion, said front portion comprising a tip; and b) first and second radiation detectors disposed within said housing at said tip, said first detector capable of detecting beta particles and gamma radiation and serving to shield said second detector from at least a portion of the beta particles detected by said first detector. While the present invention is not limited by the configuration of the detectors, in one embodiment, the first detector is positioned in front of the second detector in a manner such that gamma radiation reaching said tip of said device contacts said first detector prior to contacting said second detector.

Likewise, the present invention is not limited by the nature of the detectors. In one embodiment, the first and second detectors are semiconductor detectors. In a preferred embodiment, the semiconductor detectors are ion-implanted silicon detectors. In a particularly preferred embodiment, the semiconductor detectors are surface barrier detectors or positive intrinsic negative semiconductors. Moreover, while the present invention is not limited to the type of the detectors, in one embodiment the first and second detectors comprise circular silicon wafers of identical dimensions.

In another embodiment, the device further comprises first and second preamplifiers contained within said housing, said first preamplifier coupled to said first detector and said second preamplifier coupled to said second detector. While the present invention is not limited to a precise configuration, in one embodiment, the preamplifiers are both connected to a power supply.

In yet another embodiment, the device further comprises a radiation entrance window defining said tip and the end of the front portion of said housing. In a preferred embodiment, the radiation entrance window permits the transmission of gamma radiation and wherein the remainder of the housing blocks the transmission of gamma radiation. In such an embodiment, the radiation entrance window is preferably opaque and comprises aluminum.

The present invention also contemplates a device, comprising: a) an elongated housing, comprising a hand-graspable rear portion and a front portion, said front portion comprising a cylindrical tip; and b) first and second semiconductor radiation detectors disposed within said housing at said tip, said first detector capable of detecting beta particles and gamma radiation and serving to shield said second detector from at least a portion of the beta particles detected by said first detector.

In one embodiment, the device further comprises a radiation entrance window defining said tip and the end of the front portion of said housing. While the present invention is not limited to a specific configuration, in such an embodiment the first detector is positioned in front of said second detector relative to said radiation entrance window in a manner such that radiation reaching said tip of said device contacts said first detector prior to contacting said second detector.

The present invention also contemplates a device, comprising: a) an elongated housing, comprising a hand-graspable rear portion and a front portion, said front portion comprising a cylindrical tip having a radiation entrance window, wherein said radiation entrance window permits the transmission of gamma radiation and wherein the remainder of the housing blocks the transmission of gamma radiation; and b) first and second semiconductor radiation detectors disposed within said housing at said tip, wherein said first detector is positioned in front of said second detector relative to said radiation entrance window in a manner such that radiation reaching said tip of said device contacts said first detector prior to contacting said second detector, said first detector capable of detecting beta particles and gamma radiation and serving to shield said second detector from at least a portion of the beta particles detected by said first detector.

In another embodiment, the present invention contemplates a method for detecting radiopharmaceuticals within diseased tissue, comprising a) providing: 1) a patient having a region of diseased tissue, 2) a radiopharmaceutical capable of emitting beta particles, and 3) a device comprising a housing having a rear portion and a front portion, said front portion comprising a tip with first and second radiation detectors disposed within said housing at said tip, said first detector capable of detecting beta particles and gamma radiation and serving to shield said second detector from at least a portion of the beta particles detected by said first detector; b) administering said radiopharmaceutical to said patient; and c) detecting beta particles emitted from said radiopharmaceutical with said device within said region of said patient. The present invention is not limited by the nature of the device. However, in certain embodiments the device may have the characteristics described for the devices above.

In yet another embodiment, the present invention contemplates a method for detecting radiopharmaceuticals within diseased tissue, comprising: a) providing: 1) a patient having a region of diseased tissue, 2) a radiopharmaceutical capable of emitting beta particles and gamma radiation, and 3) a device comprising: i) an elongated housing, said housing comprising a hand-graspable rear portion and a front portion, said front portion comprising a cylindrical tip, and ii) first and second semiconductor detectors disposed within said housing at said tip, said first detector capable of detecting beta particles and gamma radiation and serving to shield said second detector from at least a portion of the beta particles detected by said first detector; b) administering said radiopharmaceutical to said patient; and c) detecting beta particles emitted from said radiopharmaceutical with said device within said region of said patient. The present invention is not limited by the nature of the device. However, in certain embodiments the device may have the characteristics described for the devices above.

In still another embodiment, the present invention contemplates a method for detecting radiopharmaceuticals within diseased tissue, comprising: a) providing: 1) a patient having a region of diseased tissue, 2) a radiopharmaceutical capable of emitting beta particles, and 3) a device comprising: i) an elongated housing, comprising a hand-graspable rear portion and a front portion, said front portion comprising a cylindrical tip having a radiation entrance window, wherein said radiation entrance window permits the transmission of gamma radiation and wherein the remainder of the housing blocks the transmission of gamma radiation, and ii) first and second semiconductor radiation detectors disposed within said housing at said tip, wherein said first detector is positioned in front of said second detector relative to said radiation entrance window in a manner such that radiation reaching said tip of said device contacts said first detector prior to contacting said second detector, said first detector capable of detecting beta particles and gamma radiation and serving to shield said second detector from at least a portion of the beta particles detected by said first detector; b) administering said radiopharmaceutical to said patient; and c) detecting beta particles emitted from said radiopharmaceutical with said device within said region of said patient. The present invention is not limited by the nature of the device. However, in certain embodiments the device may have the characteristics described for the devices above.

In another embodiment, the present invention contemplates a method for detecting radiopharmaceuticals within diseased tissue, comprising: a) providing: 1) a patient having a region of diseased tissue, 2) a radiopharmaceutical capable of emitting beta particles, and 3) a device comprising: i) a probe having a first radiation detector which generates an electrical signal in response to the passage of radiation into said first detector from a radiopharmaceutical in diseased tissue; and ii) an optical transmitter coupled to said probe for transmitting said electrical signal as an optical signal to a remote location; and b) administering said radiopharmaceutical to said patient; and c) detecting beta particles emitted from said radiopharmaceutical with said device within said region of said patient. In a preferred embodiment, the device further comprises a second radiation detector, said first detector capable of detecting beta particles and gamma radiation and serving to shield said second detector from at least a portion of the beta particles detected by said first detector.

BRIEF DESCRIPTION OF THE FIGURES

FIG. 2 illustrates a schematic diagram of the wireless probe system of the present invention incorporating infrared transmitters and receivers.

GENERAL DESCRIPTION OF THE INVENTION

Figure 1:
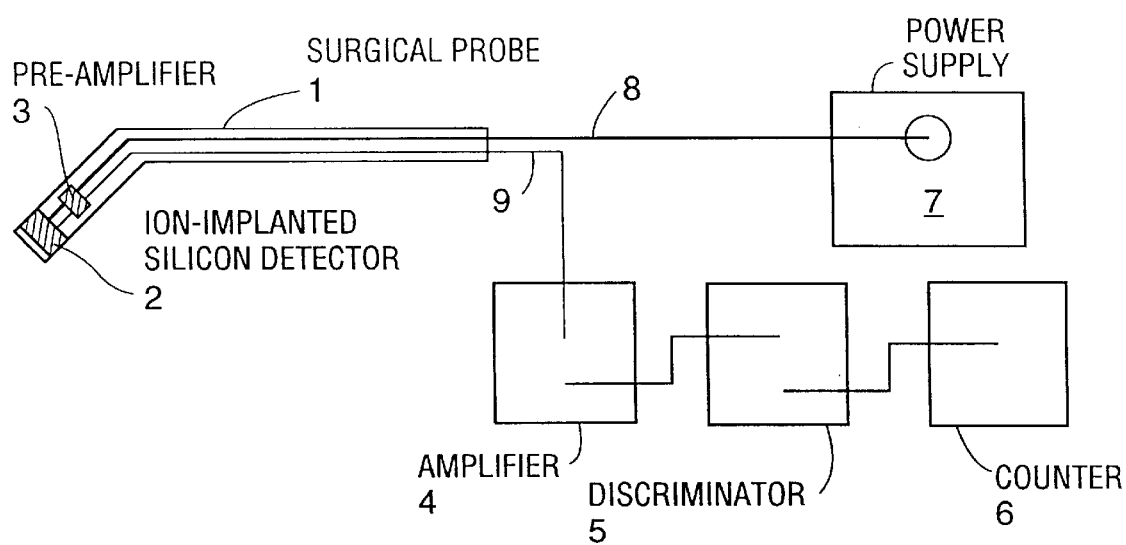
FIG. 1 illustrates a schematic diagram of the probe system of the present invention.

The present invention solves the problems presented in the prior art by providing a solid state beta-sensitive radiopharmaceutical probe incorporating an ion-implanted silicon detector (IISD), which is highly sensitive to beta particles and much less sensitive to gamma ray contamination. The use of an IISD in the probe of the present invention therefore provides an effective means for preferentially detecting beta particles over gamma radiation, while at the same time substantially minimizing the requisite size of the probe instrument itself.

I. Semiconductor-Based Detection Devices

Semiconductor-based detectors typically provide "doped" regions in materials such as silicon (Si) or cadmium telluride (CdTe), for the detection of radiation. The "doping" process involves the introduction of ions into defined areas, creating an interface between positively- and negatively-charged areas in the detection material. The thickness of the interface between the positively- and negatively-charged regions is defined as the "depletion depth", which is the active region of the detector responding to the passage of radiation particles or gamma rays. In semiconductor-based detectors, a biasing voltage is typically applied to increase the size of the active region.

However, conventional radiopharmaceutical probes employing semiconductor technology, such as the CdTe-based Neoprobe-1000™ (Neoprobe Corporation, Columbus, Ohio), are designed primarily for use as gamma detectors. In these devices the depletion depth can be as large as 5 mm, and is often located further within the detector material itself, which makes these devices highly susceptible not only to the desirable gamma rays entering through the front detector window, but also to contaminating radiation entering through the side wall of the device.

The usefulness of these gamma probes for the detection of beta-emitting radiopharmaceuticals is therefore severely limited, since several inches of additional lead shielding would have to be incorporated in order to sufficiently minimize the effects of background gamma rays and 511 kev annihilation photons. The addition of such a large amount of shielding would obviously produce an awkward and unwieldy surgical instrument, which would clearly be unsuitable for use in small surgical fields. Conventional semiconductor-based gamma detectors utilizing the lithium drift process for doping the silicon (Si(Li)) suffer from the same insurmountable problem.

One potential solution to this problem would be to incorporate another class of semiconductor detectors known as surface barrier detectors, in which the active region or depletion depth of the detector is both smaller and closer to the surface. A thinner depletion depth located closer to the surface greatly decreases the detection of unwanted gamma radiation entering from the sides of the probe, thereby substantially reducing the amount of shielding necessary to create an effective beta-sensitive radiopharmaceutical probe. The optimal depletion depth is dependent upon the particular radionuclide sought to be detected. For example, with respect to $^{18}F$, a preferred range for the depletion depth would be 100–2000 microns. In a more preferred embodiment the range is 300–1000 microns, and in a most preferred embodiment, the range is 400–600 microns.

A. Ion-Implanted Silicon Detectors

However, while surface barrier detectors are one possible candidate for use in beta-sensitive radiopharmaceutical probes, IISDs are a superior choice. The ion-implantation process utilized in the doping of these semiconductor detectors provides a more uniform depth and distribution of the doped material, which results in better energy resolution. Moreover, the placement of the electrical contacts in ion-implanted detectors also results in less statistical noise from leakage current. For example, it has been reported that IISDs produce approximately 40% less noise than surface barrier detectors at body temperature, and their operating parameters are more stable over a wider range of ambient conditions. See EG&G Ortec, *Modular Pulse-processing Electronics and Semiconductor Radiation Detectors*, p. 400 (EG&G Ortec, Oak Ridge, 1995). This significantly improves the energy discrimination capability of the probe, allowing further reduction of the photon contribution to the signal as described above.

Moreover, IISD detectors are much less prone to permanent damage than surface detectors if the detector material itself is accidentally touched or contacted by fluids, due to a tear in the detector window cover. The exposed front face of the surface barrier detectors is more susceptible to damage because the electrical contacts are placed on the surface of the detectors, in contrast with ion-implanted detectors, where the electrical contacts are deposited below the surface.

Accordingly, the use of an IISD in the probe of the present invention substantially reduces the detection of background gamma rays from distant accumulations of a radiopharmaceutical, thereby allowing a user to detect the presence of positron-emitting radiopharmaceuticals, such as $^{18}F$-labeled-Fluoro-2-Deoxy-D-Glucose (FDG), while substantially minimizing the contaminating effect of the 511 keV photons created by annihilation of the positron. It is further contemplated that similar particles such as Auger or conversion electrons could also be detected by the probe of the present invention.

In one preferred embodiment, the present invention contemplates the preferential detection of beta particles through the incorporation of a highly-selective IISD detector into the tip of a probe. When struck by a beta particle or equivalent, a small electrical current or pulse is produced in the detector. This pulse is shaped and amplified by a preamplifier, which in a preferred embodiment is placed as close to the detector as possible to reduce electrical noise. The signal then travels to an amplifier. Impedance matching with the amplifier is also performed by the preamplifier. In a particularly preferred embodiment, the signal then travels to a discriminating means, which selectively filters the gamma ray component of the amplified signal, and reduces the effect of noise, such as that caused by the leakage current, on the amplified signal. Finally, the resulting pulses are counted to give an indication to the user as to whether a significant number of beta particles are being detected.

II. Surgical Probe Utilizing Stacked Semiconductor Detectors

In another embodiment, the present invention contemplates a surgical probe having more than one semiconductor-based detector. While the present invention is not limited to the precise number of detectors utilized, in one embodiment a pair of detectors are used. In this embodiment, the detectors are configured such that one detector monitors beta particles and gamma radiation and the other detector monitors gamma radiation only. In this manner, the background gamma radiation can be quantitated and total beta particle absorbance of the first detector can be calculated (i.e., the gamma radiation is subtracted as background).

While the present invention is not limited to a particular configuration of the multiple-detector system, in one embodiment two detectors are set forth such that the first detector can detect beta particles and gamma radiation, while the second detector is shielded from beta particles but is exposed to gamma radiation. In one preferred embodiment, the dual-detector system is configured such that the second detector is shielded from the beta particles by the first detector. In this embodiment, the configuration is referred to as "stacked," and this embodiment is particularly desirable as the background gamma radiation detected by the second detector can be directly associated with the gamma radiation absorbed by the first detector. This direct associated confers an ability to subtract background gamma radiation in a highly accurate manner.

III. Applications of The Present Invention

The probe designs of the present invention are therefore useful for detecting and localizing the preferential uptake of beta-emitting radiopharmaceuticals by a lesion at the time of surgery. These probes can also be advantageously utilized to detect and localize other types of lesions, such as suspected infections or inflammatory processes, or any other disease process which can be detected by the accumulation of beta-emitting radiopharmaceuticals. Thus, a surgeon could utilize the present invention as an aid in differentiating diseased from normal tissue, and thus tailor his or her choice of tissue for resection. These probes would also assist in detecting additional diseased tissue remaining after the main tissue section has been removed, as well as searching for other regions of diseased tissue within the operative field.

Moreover, the incorporation of an ion-implanted silicon detector into the present invention, or alternatively a pair of stacked semiconductor detectors, provides a substantial size advantage in comparison with the dual probe design suggested by Daghighian et al. As a result, the intraoperative probe of the present invention can be made very small, facilitating its application to endoscopy, bronchoscopy, colposcopy, colonoscopy, cystoscopy, laparoscopy and thorascopy, as well as other forms of minimally-invasive or non-invasive surgical biopsy. In addition, the dual probe design of the present invention also represents a further significant improvement upon the dual probe design disclosed by Daghighian et al., since the present invention contemplates an embodiment comprising two identical semiconductor-based devices with the same response characteristics, thereby allowing simpler and more accurate signal correction. The dual probe disclosed by Daghighian et al. provides detectors with different shapes and volumes, and therefore different response characteristics, which requires a complicated weighted subtraction technique.

The present invention also contemplates a remote embodiment of the probe which can easily be used in almost any size surgical field. Furthermore, the probe of the present invention is very simple to operate, and as noted above does not require any special calibration procedures or signal processing in comparison with the prior art devices. Although the foregoing description has described the use of the positron-emitting radionuclide ($^{18}$F), the IISD-based probe of the present invention can also be used with more common radiopharmaceuticals labeled with $^{131}$I, $^{32}$P, and $^{111}$In, and other useful radionuclides such as $^{124}$I, $^{62}$Cu, $^{90}$Y, $^{86}$Y and $^{11}$C, as well as other beta-emitters of appropriate energy.

DEFINITIONS

In considering the present medical probe invention, some definitions are helpful. For example, an "amplifier" is an electrical circuit that amplifies an electrical signal. "Background gamma radiation" refers to unwanted gamma radiation from any source. A "counter" is any means that is able to count the number of electrical pulses it receives. A "means for discriminating" or "discriminating means" prevents a portion of an input signal from passing through the device, such as filter. For example, it is contemplated that one embodiment of the discriminating means of the present invention can selectively prevent pulses below a specific energy level from passing through. In this manner, only those signals having a pulse above a desired energy level are allowed to pass through. A "pre-amplifier" is an electrical circuit having a high gain for amplifying a weak or small signal.

"Infrared transmitter" refers to any transmitter capable of converting an electrical signal into an infrared signal and transmitting the infrared signal. "Infrared receiver" refers to any receiver capable of receiving an infrared signal containing data and converting the data into an electrical signal. "Optical transmitter" refers to any transmitter capable of converting an electrical signal into an optical signal and transmitting the optical signal. "Optical receiver" refers to any receiver capable of receiving an optical signal and converting the signal to an electrical signal.

"Radio transmitter" refers to any transmitter capable of converting an electrical signal into a radio signal and transmitting the radio signal. "Radiopharmaceutical" refers to a pharmaceutical compound with a radionuclide. It can also be referred to as a radiolabelled compound. "Radio receiver" refers to any receiver capable of receiving a radio signal and converting the signal to an electrical signal. "Wire means" refers to any means capable of transmitting data (i.e. wires, cables, and fiber optics.)

A "semiconductor detector" is a silicon chip device that can absorb beta particles and other radiation and emit a signal based upon such absorbance. An "ion-implanted silicon detector" is a silicon substrate doped with ions from a low energy accelerator for converting received beta particles into electrical signals. A "surface barrier detector" is a semiconductor detector formed by doping the silicon through a drifting process wherein the silicon is exposed to a gas of the doping material thereby introducing the doping material to the silicon. "Circular silicon wafers" are substantially flat semiconductor detectors with a circular shape.

"Stacked" refers to the configuration of more than one detector such that one detector shields another detector from at least a portion of radiation emitted from a sample. In one preferred embodiment, a dual-detector system is configured such that a second detector is capable of detecting gamma radiation, but is shielded from the beta particles by a first detector.

A "Preamplifier" is a device capable of detecting a signal (e.g., electrical impulse) from a radiation detector (e.g., an ion-implanted silicon detector or a semiconductor detector) and strengthening this signal.

A "housing" is a container capable of enveloping one or more of the components of the present invention, and an "elongated housing" refers to a housing that has a length such that a portion may be placed in a body while another portion of the same housing remains outside the body. A housing with a "radiation entrance window" has a portion of the housing that permits more radiation (e.g., beta particles and/or gamma radiation) to pass than does the rest (i.e., remainder) of the housing. It is preferred that the housing is constructed such that it blocks substantially all (preferably more than 75%, more preferably 90%) of the transmission of gamma radiation and beta particles. Such a housing may be constructed of stainless steel, plastic or carbon fiber.

An item that is "hand graspable" is dimensioned such that it can fit in a human hand.

DETAILED DESCRIPTION OF THE PREFERRED EMBODIMENTS

The following description serves to illustrate certain preferred embodiments and aspects of the present invention and is not to be construed as limiting the scope thereof.

FIG. 1 illustrates a schematic diagram of one embodiment of the radiopharmaceutical probe of the present invention. In this embodiment, a single IISD 2 is located in the tip of the probe 1 to provide an electrical signal in response to received beta particles from a radiopharmaceutical accumulated within a region of diseased tissue. As detailed above, IISDs are superior for this particular application because of their high positron to photon ratio. In other words, they have a high sensitivity to beta particles in comparison to gamma radiation.

In one embodiment, a preamplifier 3 is coupled to the detector 2 for amplifying and shaping the electrical signal into an appropriate voltage pulse. Ideally, the preamplifier 3 is located as close to the detector as possible in order to reduce electrical noise. An amplifier 4 is then coupled to the preamplifier for further amplifying the electrical signal. In a preferred embodiment, a means for discriminating a component of the electrical signal 5 is coupled to the amplifier 4 for further filtering of noise and to reduce the gamma ray component of the electrical signal. A counter 6 is coupled to the discriminator 5 for counting the received beta particles. Finally, a power supply 7 is coupled to the preamplifier for supplying power to the probe.

It should be noted that while the different circuit elements described above have been listed as separate elements and illustrated in the figures as separate hardware elements, it may be possible for them to be combined together. Furthermore, it may be possible to provide software running on a processor which performs the same functions. Therefore, the present invention is not limited to strictly hardware elements, but may comprise a combination of hardware and software.

In operation, a patient having a body part with a suspected diseased tissue is administered a radiopharmaceutical. After the radiopharmaceutical accumulates in the diseased tissue, the probe is placed in close proximity to the diseased tissue. Beta particles emitted from the radiopharmaceutical accumulated in the diseased tissue are detected by the detector 2, which generates corresponding electrical signal or pulse. Gamma radiation produced by the radiopharmaceutical either directly or by annihilation may also be detected by the detector 2. The electrical signal therefore comprises a component corresponding to the detected beta particles and a component corresponding to the detected gamma radiation. The electrical signal is then amplified first by the preamplifier 3, and then by amplifier 4.

In a preferred embodiment, the amplified signal then passes through a discriminating means 5 acts as a filter to prevent that portion of the electrical signal (or those electrical pulses) below a certain energy level from passing through. Ideally, the discriminating means provides a circuit for adjusting the detection threshold energy of the IISD, in order to balance the sensitivity of the detector with the elimination of unwanted background radiation and noise.

Finally, the signal is passed through a counter which counts the pulses present in the electrical signal. These pulses generally correspond to the number of beta particles detected by the detector 2, although it is possible that some of the pulses resulting from beta particles striking the detector may be filtered by the discriminating means 5, and that some stray gamma pulses may also pass through. However, the majority of the remaining pulses should correspond to the detected beta particles.

Based on the received beta particle count, a user can localize radiopharmaceuticals accumulated within a region of diseased tissue, such as a tumorous lesion. This localization can be performed by determining a threshold level of beta particles which indicates the presence of a lesion. In one embodiment, localization is performed by calculating a "Z-score" which indicates the beta particle count. The Z-score is calculated as:

$$\text{Z-score} = [(\text{measured particle count}) - \text{reference}]/\text{STD}$$

where the reference is determined by placing the probe at a location remote from the region suspected of having the diseased tissue. This reference indicates the background radiation emitted by the patient where no diseased tissue is present. The measured particle count is the count of the received particles by the probe at the region suspected of having diseased tissue. The difference of these two values is then divided by the standard deviation (STD) reference count, which is the standard deviation for a series of counts over the remote reference area. Regions having a Z-score of at least two to three indicate the presence of a radiopharmaceutical-avid diseased tissue. When the probe 1 is in close proximity to a tissue emitting a sufficient number of beta particles, an audio or visual signal can be activated to alert the user.

In an alternative embodiment (not shown), the remote elements (4–7) can be housed completely within the probe 1. In this embodiment, the power supply could be a battery housed within the probe housing.

In the alternative preferred embodiment illustrated in FIG. 2, the wire means 8 and 9 can be substituted with an optical transmitter 11 and receiver 10 (i.e. infrared) thereby providing greater ease of use. Optical transmitters and receivers incorporating, for example, infrared light, are well known in the art and readily available. For example, suitable components could be purchased from NEC Optoelectronics and easily incorporated into the probe of the present invention. Therefore, the optical components will not be discussed with any specificity.

The electrical signal output from the discriminator 5 is converted by the optical transmitter 11 to an optical signal for transmission to a remote receiver 10, which converts the optical signal back into an electrical signal within the means for processing 13. Here, the electrical signal is processed by counter 6. It should be apparent to one skilled in the art that the electrical signal generated by the detector 2 can be transmitted from the probe 1 at any point. In other words, the optical transmitter 11 can also be positioned immediately after the preamplifier 3, so that the amplifier 4, discriminating means 5 and counter 6 are all located within the means for processing 13. Alternatively, the infrared transmitter 11 can be located after the amplifier 4 so that the discriminating means 5 and counter 6 are both located remotely from the probe 1. It should be noted that because the probe will be "wireless" it will require an internal power supply such as battery 12 illustrated in FIG. 2.

In an alternative preferred embodiment (not illustrated), the optical transmitter and receiver can be substituted with a radio transmitter and receiver. Again, the radio transmitter can be located at different points similarly to the optical transmitter.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); kg (kilograms); $\mu$g (micrograms); L (liters); ml (milliliters); $\mu$l (microliters); cm (centimeters); mm (millimeters); $\mu$m (micrometers); nm (nanometers); °C. (degrees Centigrade); sec (seconds); msec (milliseconds); kBq (kiloBecquerels); mBq (milliBecquerels); MBq (megaBecquerels); STD (standard deviation); SUV (standard uptake values); keV (kiloelectronvolt); cps (counts per second).

EXAMPLE 1

Comparison of IISD Probe with Scintillation Probe

The ion-implanted-silicon detector used in this example was manufactured by EG&G Ortec (Ultra™: Model Number U-013-050-500; Oak Ridge, Tenn.). The detector chosen possesses a nominal 500 $\mu$m thick depletion layer and operates at 100 volts. This amount of silicon is sufficient to stop most of the positrons emitted by $^{18}$F. The factory-specified beta energy resolution of this device is 4.2 keV. The circular silicon wafer which makes up the sensitive area of the device has a diameter of 8 mm.

In the embodiment of the probe used for the present experiment, the detector unit was mounted in a light-tight aluminum cylinder. The entrance window consisted of a thin (1.27×10$^{-3}$ cm thick) sheet of aluminum foil; the cap on the other end of the cylinder contained the electrical feed through necessary for providing the biasing voltage to the device. Current pulses were conditioned with an EG&G Ortec Model 142 charged-coupled preamplifier. The length of cable between the detector and preamplifier was minimized to help reduce noise and maintain good energy resolution. Amplification of the pre-amplified pulses was performed with an EG&G Ortec Model 572 shaping amplifier (shaping time=0.5 $\mu$s). The resulting voltage signals were routed to an EG&G Ortec Model 583 pulse-height discriminator and the pulses created by the discriminator were counted by an EG&G Ortec Model 772 scaler module. A high voltage EG&G Ortec Model 556 power supply was also incorporated to feed power to the probe.

Many of the operating characteristics of the IISD were then compared to those possessed by a plastic scintillation probe tested by the present inventors in preclinical studies of FDG-guided breast cancer surgery. See Raylman et al., *J. Nucl. Med.* 36:1869–1874 (1995). Briefly, this scintillation probe consisted of a cylinder of BC-408 (Bicron Corp; Newbury,Ohio) plastic scintillator (diameter=8.4 mm; length=4 mm) fiber optically coupled to a photomultiplier tube (XP-1911; RCA Electronics). The plastic scintillator was enclosed in a stainless steel tube with a slanted front end piece to facilitate use in surgical procedures. The device further employed energy discrimination in an attempt to reduce the effect of background photon detection.

Energy Spectra

The combined positron and annihilation photon energy spectrum measured by each detector was acquired by centering the detectors 0.4 mm above a circular (8 mm diameter) piece of filter paper containing 37 kBq of $^{18}$F. Output from the amplifiers were "pulse-height analyzed" for 20 seconds by a Canberra Series 30 Multichannel Analyzer (Canberra Nuclear; Meriden, Conn.). A pure positron energy spectrum was obtained by covering the filter paper with a 0.2 mm thick piece of stainless steel, and the Multichannel Analyzer was then set to subtract mode and a 20 second acquisition performed. The stainless steel prevented positrons from reaching the detector, and thus the annihilation photon signal was subtracted from the previously measured combined spectrum, resulting in a pure positron energy spectrum. Detected photon energy spectra were obtained by acquiring a spectrum for 20 seconds with the stainless steel in place.

Figure 3A:
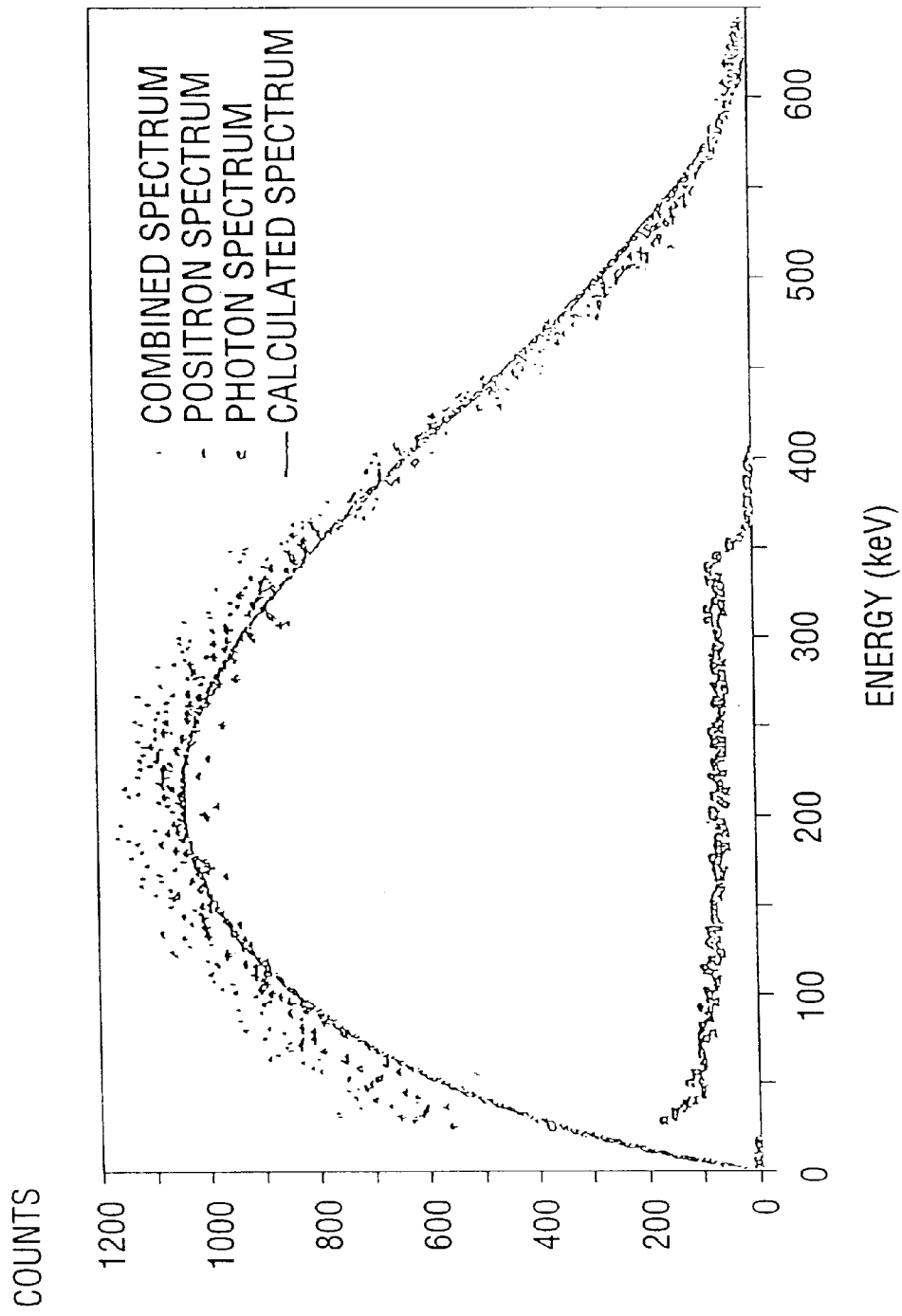
FIG. 3A illustrates a graph of the energy spectra measured using an IISD.
Figure 3B:
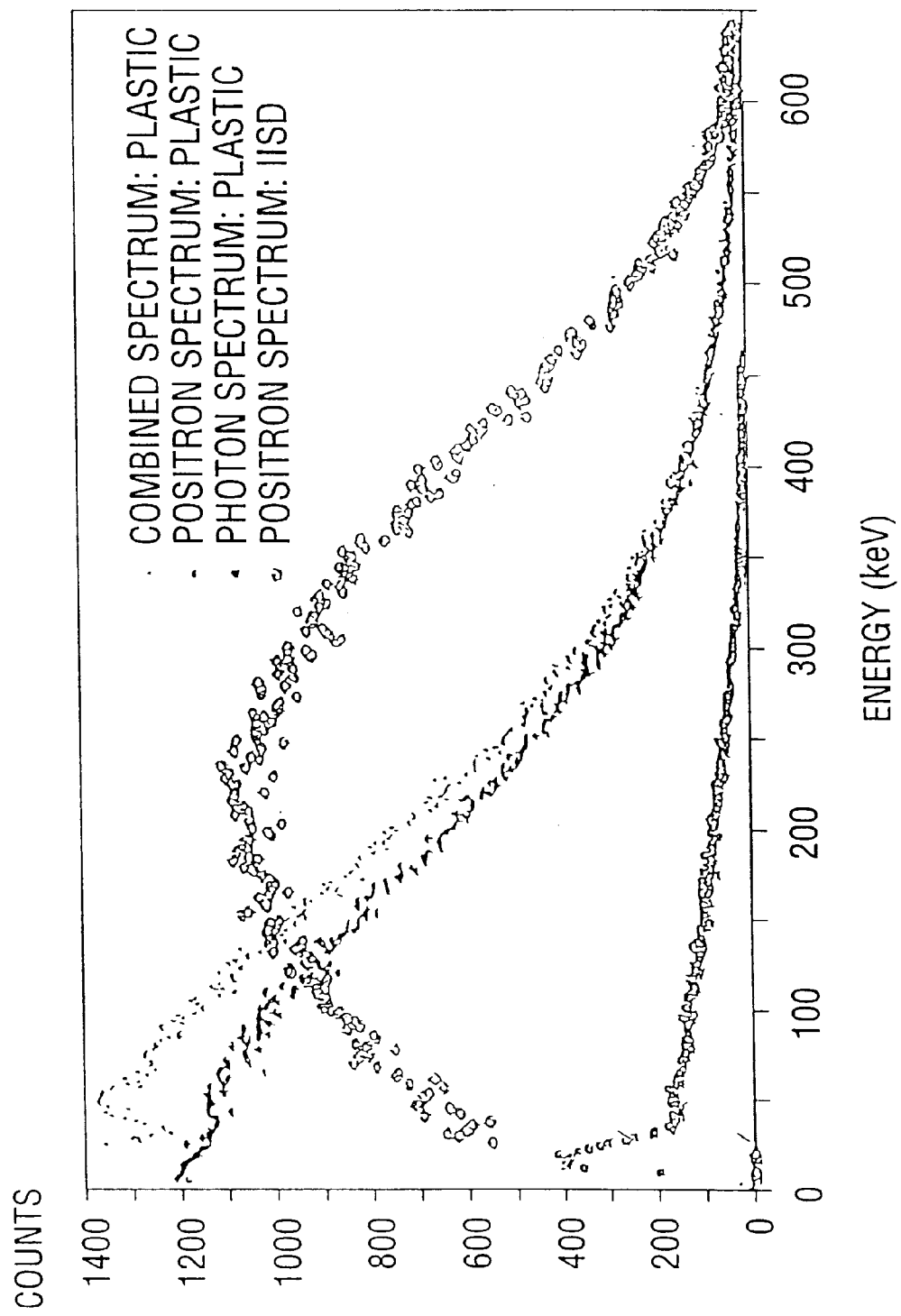
FIG. 3B illustrates the energy spectra measured using a plastic scintillator detector.

FIGS. 3A & 3B illustrate the $^{18}$F positron and 511 keV photon energy spectra obtained with the IISD and plastic scintillator detectors. FIG. 3A also shows the theoretical shape of the positron energy spectrum calculated from the Fermi theory of beta decay. See R. D. Evans, *The Atomic Nucleus* 3rd ed., pp. 278–279 (McGraw-Hill, New York, 1976). The two positron energy spectra obtained with the IISD presented in FIG. 3A illustrate that there is very little annihilation photon contamination of the combined spectrum. This is demonstrated by the very minor differences between the combined and positron spectra. Also note that the minor differences in the spectra vanish at energies above the position of the Compton edge (0.7 keV). In addition, the excellent energy resolution of the IISD is evident from the good agreement between the measured and calculated positron energy spectra. FIG. 3B shows the energy spectra from the plastic scintillator detector in addition, for the sake of comparison, to the positron spectrum obtained with the IISD. Clearly, the positron energy spectra acquired with the plastic scintillator are distorted compared to the IISD spectrum. These spectra appear to have an overabundance of lower energy events.

Since energy discrimination of the signals from the detector is used to reduce photon contamination, the positron and photon energy spectra measured by the detector are important. The spectra in FIG. 3A demonstrate the very good response of the ion-implanted silicon detectors to positrons and annihilation photons. It is important to note that measured positron energy spectrum agrees very well with the positron energy spectrum calculated for $^{18}$F. Thus, it seems that very little energy is lost in the window of the detector. In addition, the position of the Compton edge measured by the IISD correlates reasonably well with the calculated value of 340.7 keV for 511 keV photons.

While FIG. 3A demonstrates the very good performance characteristics of the IISD, the energy spectra in FIG. 3B illustrates that the problems with the plastic scintillator detector. The positron spectrum appears distorted and skewed towards the low energy end of the scale, compared to the IISD spectrum, thus indicating that not all of the scintillation light from each event is being collected. There are several additional possible sources of light loss in the system. First, some of the light pulses undergo numerous reflections from the walls of the scintillator, and, although reflective coatings were applied, many reflections might produce some attenuation of signal. Also, there is a slight mismatch between the indices of refraction of the optical coupling compound and the scintillator. The index of refraction of the optical coupling compound is 1.46 and that of the scintillator is 1.58. The critical angle for total internal reflection, therefore, is 67.5°. Hence, some of the light signals are not coupled to the fiber optic cable. The photon spectrum seems also to be affected by inefficient light collection in a fashion similar to that of the positron spectrum.

Spatial Resolution

The spatial resolution of the IISD was measured by translating a 2.54×10$^{-2}$ mm thick piece of thread soaked in $^{18}$F (15.5 kBq) across the face of the detector. The distance between the detector and thread was 0.4 mm. At each point a series of five, five second acquisition was obtained; a mean count rate and standard deviation for each position was calculated from this data. The resulting curve of count rate versus position was fit to a Normal distribution and the full width at half maximum (FWHM) extracted as a measure of resolution. Measurements of resolution were acquired for a number of different threshold energies ranging from 6.8 keV to 495 keV.

To determine the effect of background radiation on the resolution of the IISD, a large circular petri dish containing 1.55 MBq of $^{18}$F (5.2 kBq/ml) (this concentration simulates an SUV of 1 for an assumed injection of 370 MBq to a 70 kg patient one hour prior to the surgical procedure) was placed behind the thread. The same method for acquiring and processing data to calculate resolution was performed.

Figure 4:
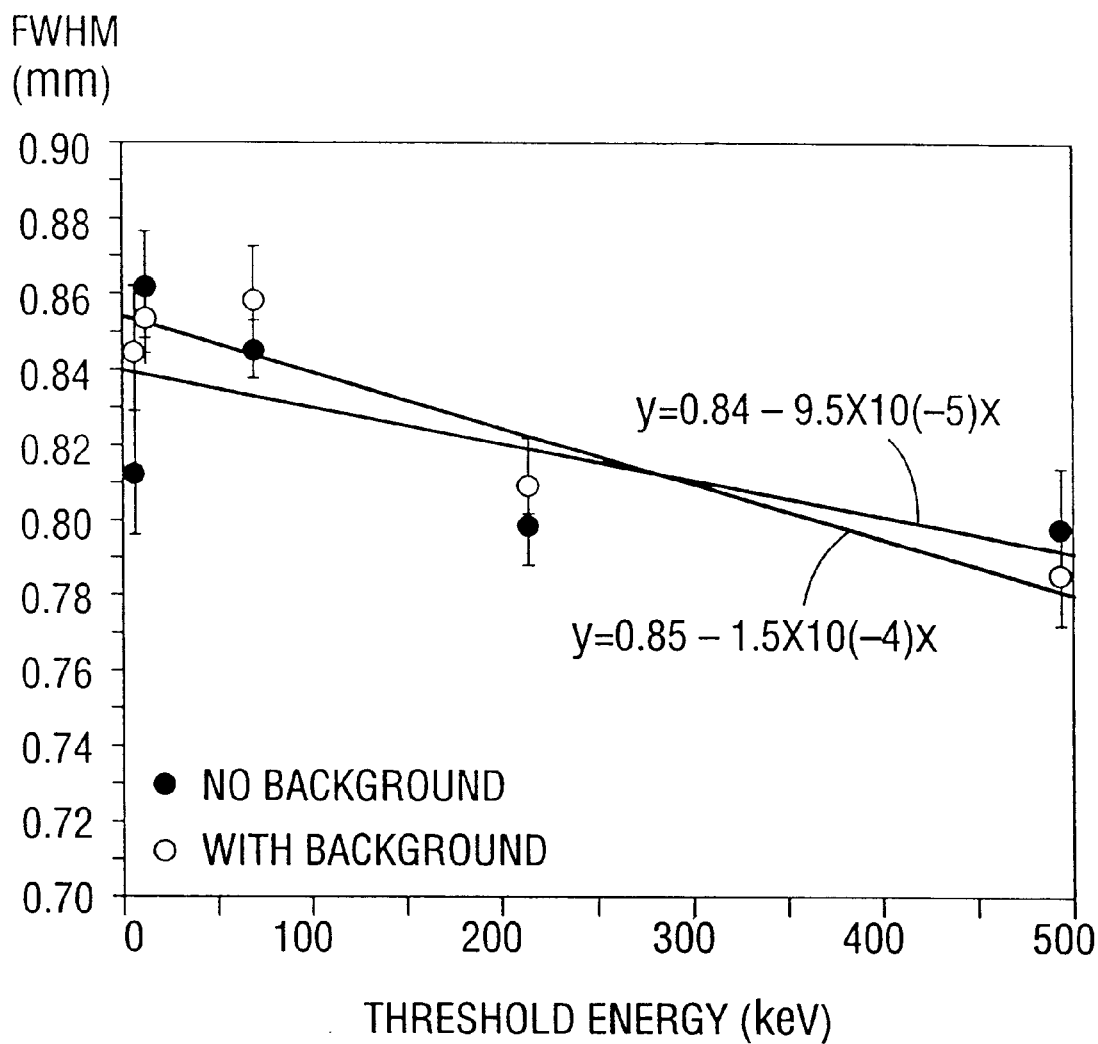
FIG. 4 illustrates a graph showing resolution of an IISD versus a threshold energy setting.

FIG. 4 illustrates the change in IISD detector resolution as a function of energy threshold. Both curves, with and without the presence of background annihilation photon flux, are relatively flat; indicating a minimal dependence of resolution on threshold energy. In addition, the fact that the two curves are so similar supports data displayed in FIG. 3A that very little photon contamination of the positron signal is present.

The effect of background photon contamination on IISD resolution appears to be minimal. The data presented in FIG. 4 indicates that the change in spatial resolution as a function of energy threshold remains virtually unchanged; even when an annihilation photon background flux representative of that anticipated in a normal human upper chest is added. This is an improvement over other plastic scintillation detectors which use energy discrimination to remove background contamination. See R. Raylman et al., *J. Nucl. Med.* 35:909–913 (1994).

Sensitivity and Selectivity

To measure detection sensitivity, a disk of filter paper (8 mm diameter) containing 55.5 kBq of $^{18}$F was positioned 0.4 mm below the front face of the IISD. A series of five, five second acquisitions were obtained from which mean and standard deviation counts per second were calculated. A second series of measurements, measuring only photon interactions, were obtained following the placement of a 0.2 mm thick piece of stainless steel in front of the detector face.

By dividing the results from the first set of measurements by the amount of activity present on the disk, the combined (positron and photon) sensitivity was calculated. The positron sensitivity was calculated by first subtracting the pure photon count rate from the combined count rate and dividing by the amount of activity on the disk. Finally, the photon sensitivity was calculated by dividing the pure photon count rate by the amount of activity on the disk. The ability of the detector to distinguish between positron events and photon events, or its "selectivity," was determined by dividing the pure positron sensitivity by the photon sensitivity. All parameters were determined at energy thresholds ranging from 6.8 keV to 635 keV. Both sensitivity and selectivity were determined for the IISD and plastic scintillation probe.

Figure 5A:
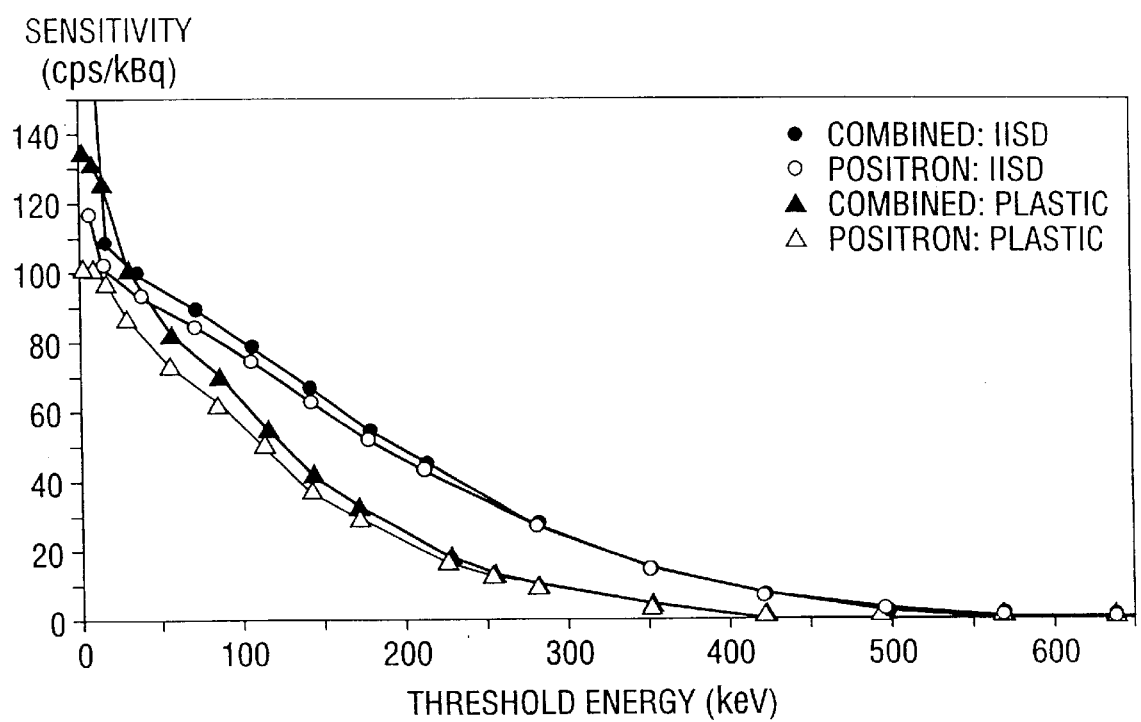
FIG. 5A illustrates a graph showing the detection sensitivity for positrons versus threshold settings. This displays data acquired with both an IISD and a plastic scintillator.
Figure 5B:
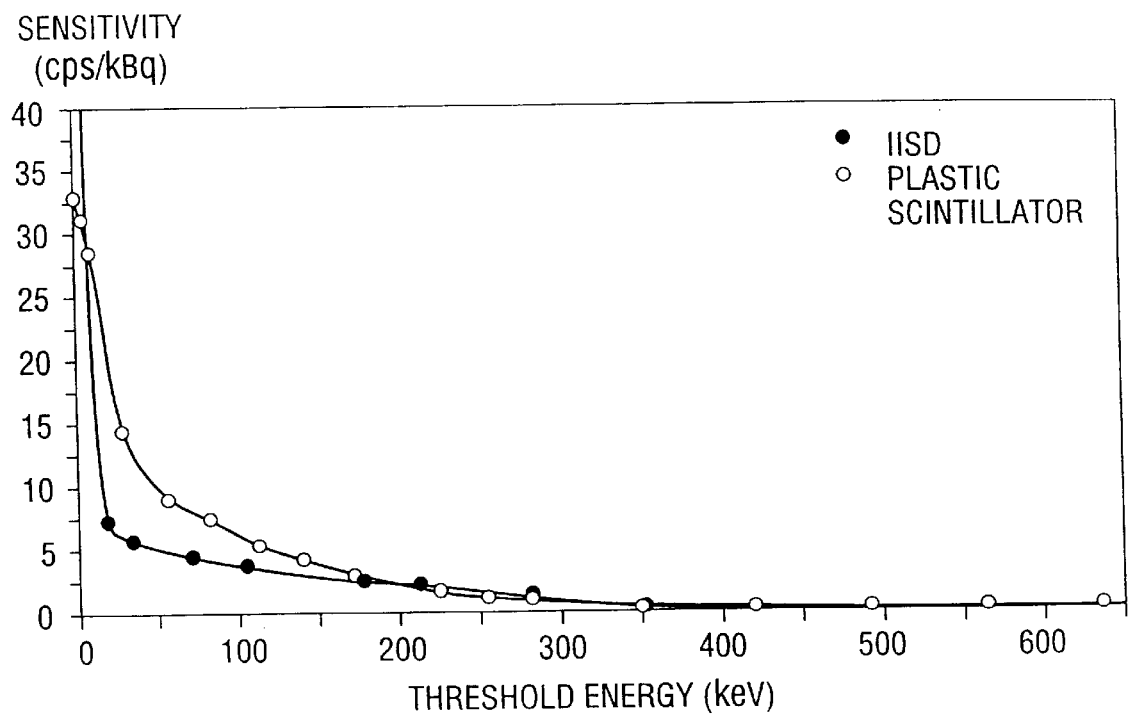
FIG. 5B illustrates the detection sensitivity for 511 keV photons versus threshold energy settings. This displays data acquired with both an IISD and a plastic scintillator.

The plot in FIG. 5A compares the combined and positron sensitivities measured with the IISD as a function of threshold energy to the sensitivities measured with the plastic scintillator. Note that at most threshold energies the IISD has a higher positron detection sensitivity than the plastic scintillator. The graph in FIG. 5B demonstrates that the plastic scintillator has a higher photon detection sensitivity than the IISD at most threshold energies. The combination of a high positron detection sensitivity and low photon sensitivity results in a very high detected positron-to-photon ratio (selectivity) for the IISD, as demonstrated by the plot in FIG. 6.

Detection sensitivity is at least as important of an operating characteristic as is resolution. The data shown in FIG. 5A reveals the excellent sensitivity of the IISD detector. Indeed, at an energy threshold of 14 keV, combined detection sensitivity is 108.7 cps/kBq, which is virtually identical to that reported by Daghighian et al. (108.0 cps/kBq) for the dual plastic scintillation probe. At this threshold energy, the pure positron sensitivity is 101.3 cps/kBq. As expected, detection sensitivity decreases rapidly as the energy threshold is increased. But, because of the peaked shape of the plastic scintillator energy spectrum the reduction in sensitivity as a function of energy threshold is steeper than for the IISD. This effect is most prominent at low threshold energy values. Combined signal sensitivity is also greater than pure positron sensitivity due to detection of signals from annihilation photons.

The difference between combined and positron sensitivity is most pronounced in the data from the plastic scintillator. The large disparity is due mostly to the higher photon detection cross section of the plastic scintillation detector compared to the IISD, as demonstrated by the data presented in FIG. 5B. Sensitivity to photons can be reduced by using a thinner piece of plastic scintillator. For total absorption of all of the positron emitted by $^{18}$F the piece of scintillator must be at least 2 mm thick.

However, a disadvantage of using a thin piece of scintillator is the increased probability that positrons not directed normal to the front surface can escape through the side of the detector before depositing all of their energy; further reducing the amount of light collected per event. A thinner detector will also reduce the detection cross section of photons originating from areas located to the sides of the detector. The presence of sources of radiation which are not parallel to the face of the probe is common in situations where the device is used to survey a tumor bed. These regions are usually concave and therefore the probe will be presented with a flux of positrons and photons from the side. While proper shielding can eliminate the effect of positron flux, the photon flux is very difficult to shield so the geometry of the detector itself must be optimized to reduce detection. Since the IISD has a much thinner active area (500 μm in this case) than most scintillation detectors, the detection of "off-axis" source of photons will be reduced significantly; making IISDs superior for use in surgical applications.

Figure 6:
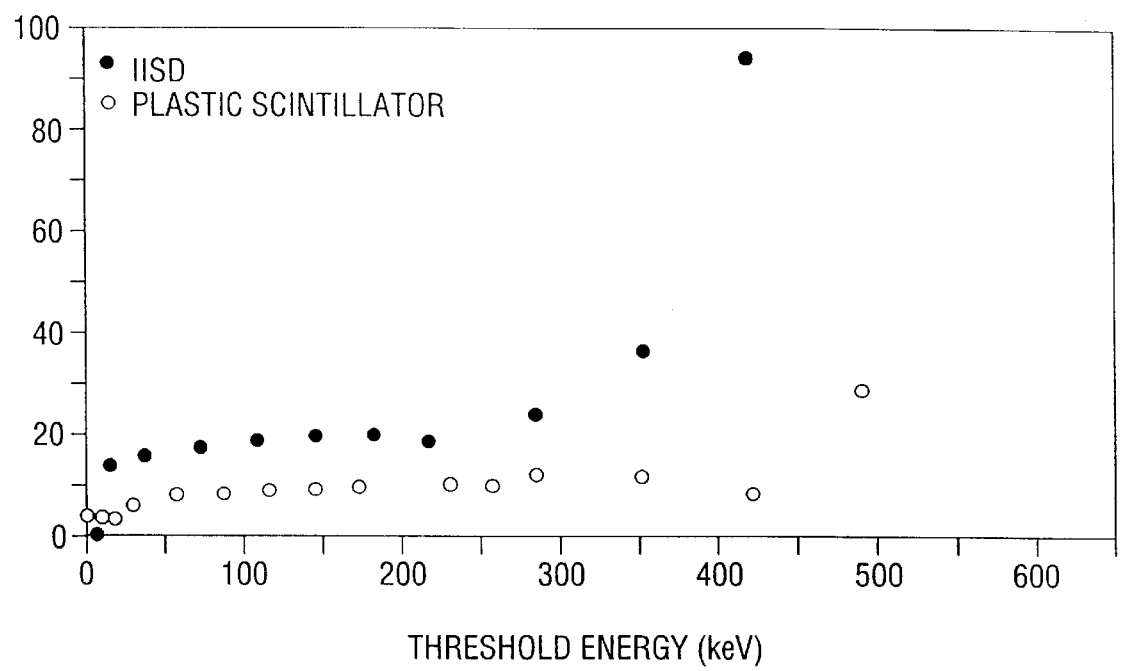
FIG. 6 illustrates the positron/photon detection ratio versus threshold energy.

Perhaps the most important operating characteristic of a positron sensitive detector for use in FDG-guided procedures is the ratio of detected positron-to-photon events. FIG. 6 shows the ratio between positron and photon sensitivity as a function of threshold energy. The differences in the data for the IISD and plastic scintillator at the lower and intermediate threshold energies are due to the higher photon detection cross section and lower positron sensitivity of the plastic scintillator detector at these energy threshold settings. At higher energies, the positron/photon ratio for the plastic detector doesn't increase at the same energy as the IISD because even though the amount of photons detected has been reduced almost to zero; this is because the lower positron sensitivity at higher energies forces the ratio to stay small until absolutely no photons are detected and then the selectivity rises rapidly.

The data presented in FIG. 6, in conjunction with the data displayed in FIG. 5, can be used to determine the optimal threshold energy setting for the IISD. Clearly, a trade-off in operating characteristics must be made. From FIG. 5 we see that the greatest sensitivity is achieved at very low threshold settings. This phenomenon is due to the detection of annihilation photons and noise present in the detector. Therefore, the selectivity should be poor, this is confirmed by the data shown in FIG. 6. Also we see from FIG. 6 that, because of the complete exclusion photon events, selectivity is greatest at threshold energies above ~350 keV. However, because of the large overlap of the photon and positron energy spectra, illustrated by the plots in FIG. 3A, sensitivity at these settings is poor. Therefore a compromise must be made. Since the positron/photon ratio is relatively constant from a threshold energy of 14 keV to 211 keV, the threshold setting which results in the greatest sensitivity was chosen, 14 keV.

EXAMPLE 2

Simulation of Surgical Field Following Excision

To test the effectiveness of the IISD in a search for the presence of residual diseased tissue left in the surgical field following attempts at excision, a surgical field following attempted lesion excision was simulated. Differing amounts of residual tumor were modeled by soaking various sized disks (2 mm, 5 mm, 10 mm and 15 mm diameter) in a solution of $^{18}$F (concentration=22.2 kBq/ml; simulating an SUV of 4.2 assuming a 370 MBq infusion and a 70 kg patient). To model exposed normal tissue present in the tumor bed, a piece of filter paper (7 cm×3 cm) was soaked in a solution of $^{18}$F (concentration=5.2 kBq/ml; simulating an SUV of 1, assuming a 370 MBq infusion and a 70 kg patient) and mounted on similar sized piece of tissue equivalent plastic (Gammex/RMi; Madison, Wis.).

In order to simulate the background photon signal emanating from distant areas of normal tissue, a large petri dish (volume=300 ml, diameter=14 cm) was filled with a solution of $^{18}$F (concentration=5.2 kBq/ml; simulating an SUV of 1 assuming a 370 MBq infusion and a 70 kg patient). The large piece of filter paper and the piece of tissue equivalent plastic it was mounted on were placed on top of the petri dish. The disks simulating the tumor residue were then placed (one at a time) in the center of the large sheet of filter paper.

A series of five, 5-second measurements were acquired while the probe was positioned 0.4 mm above the petri dish, the large piece filter paper and the small disk of filter paper. Readings were acquired at a threshold energy of 14 keV. Mean and standard deviations calculated from this data were used to determine the Z-scores of the readings acquired above the large piece of filter paper (normal tissue) and the small disks (residual tumor), relative to the petri dish (sources of distant background) measurements. This experiment was repeated using the plastic scintillator probe.

Figure 7A:
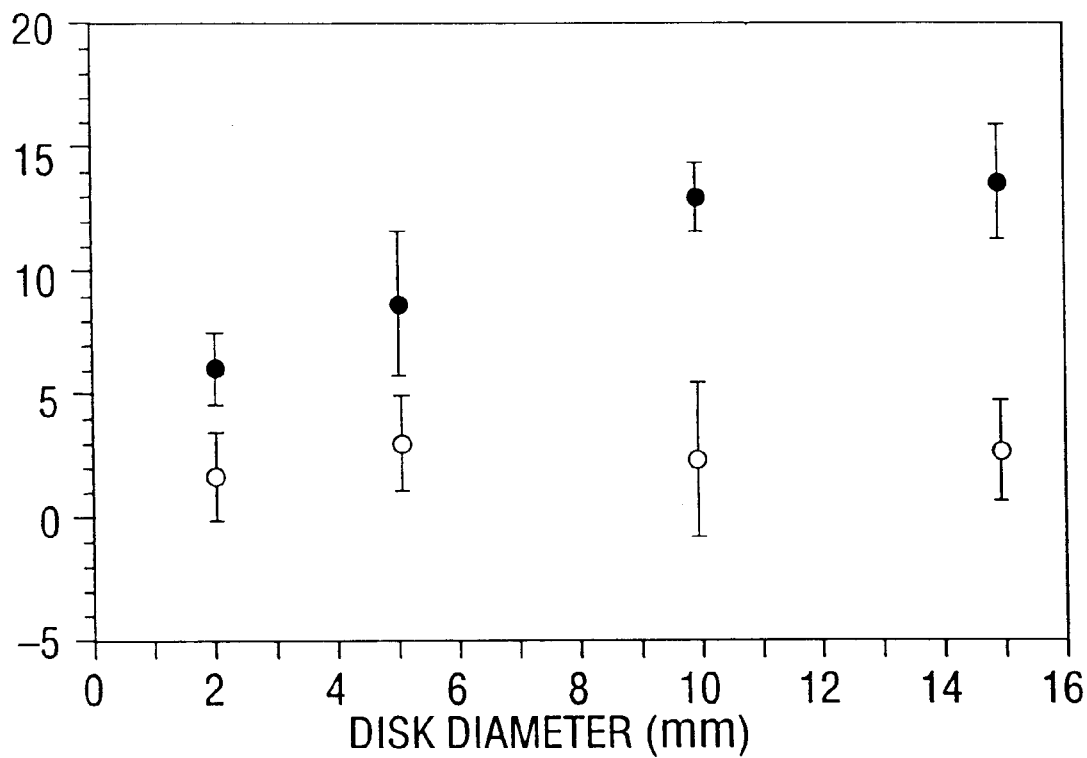
FIG. 7A illustrates the Z-score versus disk diameter. Measurements were made with an IISD and a threshold energy setting of 14 keV. The hollow circle indicates the surrounding paper while the dark circle indicates the small disk.
Figure 7B:
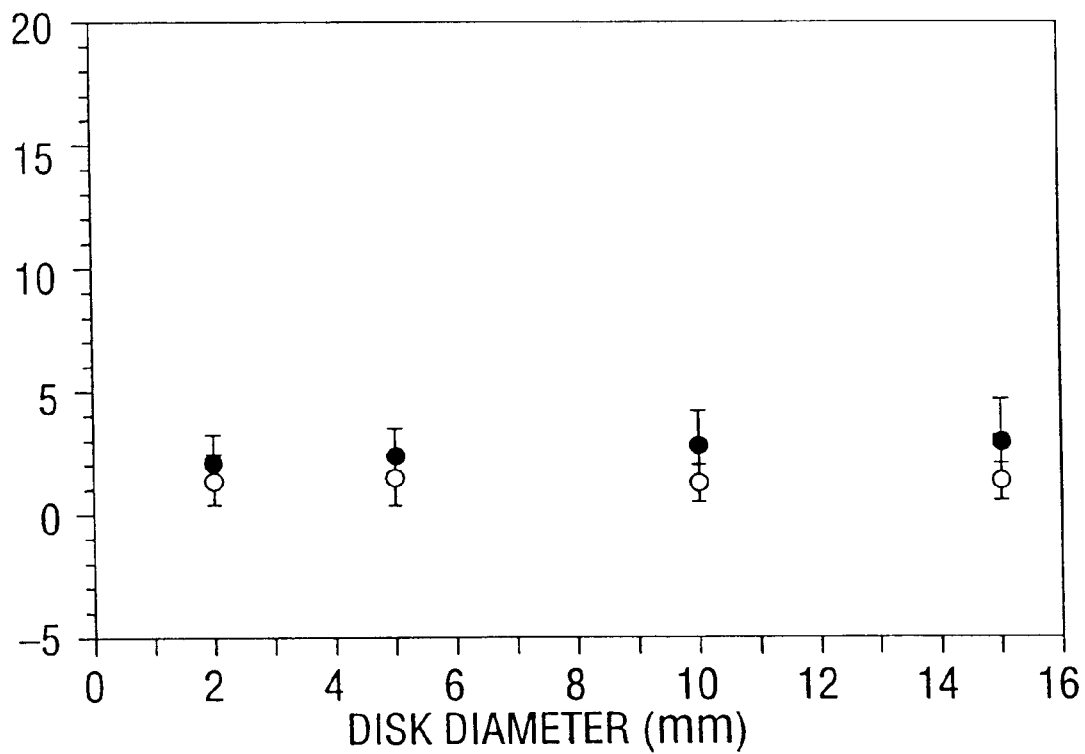
FIG. 7B illustrates the Z-score versus disk diameter. Measurements were made with a plastic scintillator probe and a threshold energy setting of 170 keV. The hollow circle indicates the surrounding paper, while the dark circle indicates the small disk.

The plot in FIG. 7A shows the results of this experiment to determine if it is possible to locate simulated residual FDG-avid disease in a tumor bed. Graphs of Z-scores versus disk size for the cases where the IISD detector was placed above the simulated tumor bed and above the simulated residual tumor are displayed. The plot in FIG. 7B shows the results for the plastic scintillator, with the energy threshold at 170 keV. At energy threshold below 170 keV signal from the disks of activity were completely indistinguishable from background.

Having decided upon the optimal energy threshold value for the IISD, the use of this detector in a simulated search for tumor remnants was performed. The data shown in FIG. 7A demonstrates the potential effectiveness of this device in this application. Even when the amount of $^{18}$F and the disk were smallest (2 mm and 0.52 kBq [14 nCi], respectively), the Z-score was greater than simulated surrounding tissues. As the disk and total amounts of activity grew, the Z-score relative to the simulated background activity grew, until the disk size exceeded the diameter of the detector (8 mm). At the point where the diameter of the disk was greater than the detector, those positrons and photons not emitted from the areas viewed by the IISD were not detected; hence the static Z-score for the 15 mm diameter disk. While the IISD was able to detect the disks of activity in the presence of realistic sources of background, the plastic-scintillator probe had a great deal of difficulty in accomplishing this task. Indeed, in order to approach the performance of the IISD, the energy threshold had to be set to 170 keV. At this level the sensitivity to positrons was measured to be 29.4 cps/kBq, in contrast the IISD's positron sensitivity at 14 keV (the level utilized in the experiment) is 101.3 cps/kBq.

EXAMPLE 3

Utilizing Stacked Detectors

Figure 8:
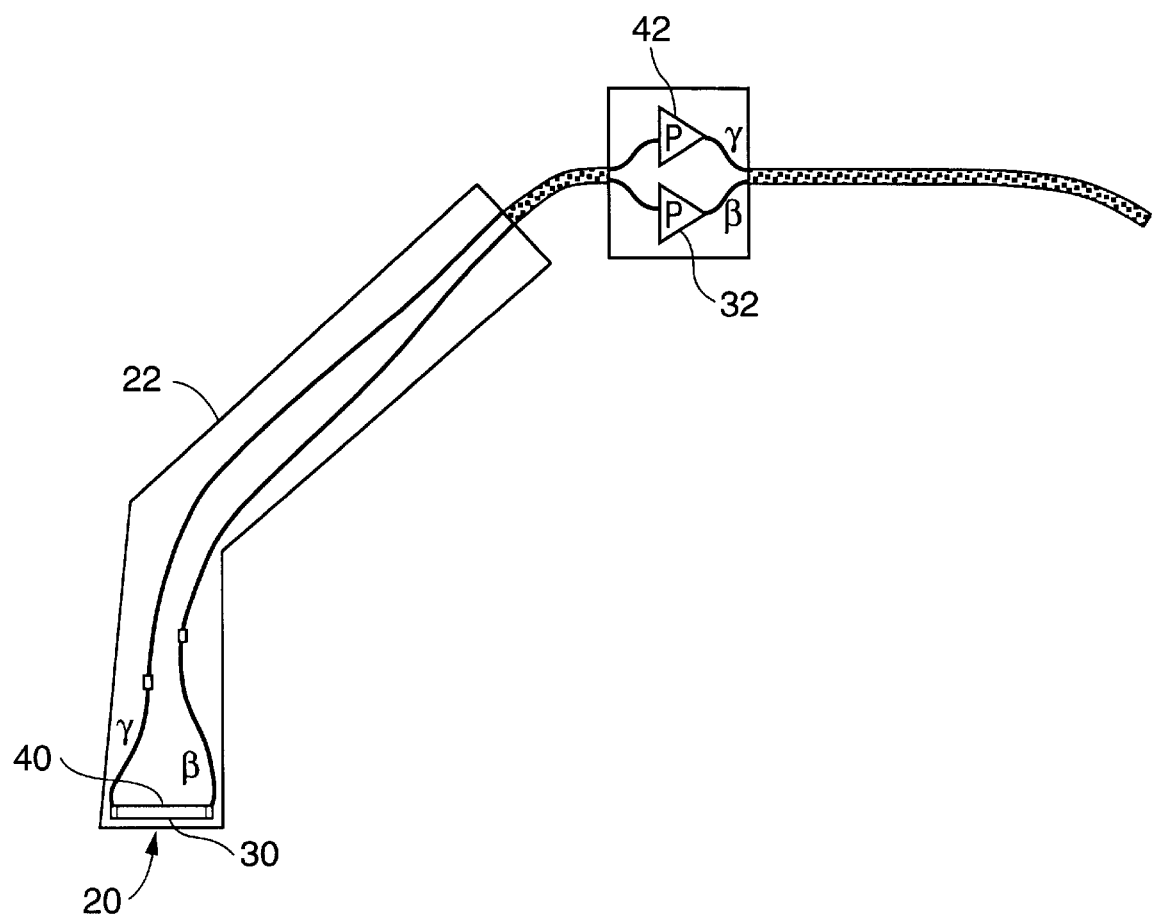
FIG. 8 illustrates another preferred embodiment of the device of present invention, utilizing two semiconductor-based detectors stacked in the tip of a probe.
Figure 9:
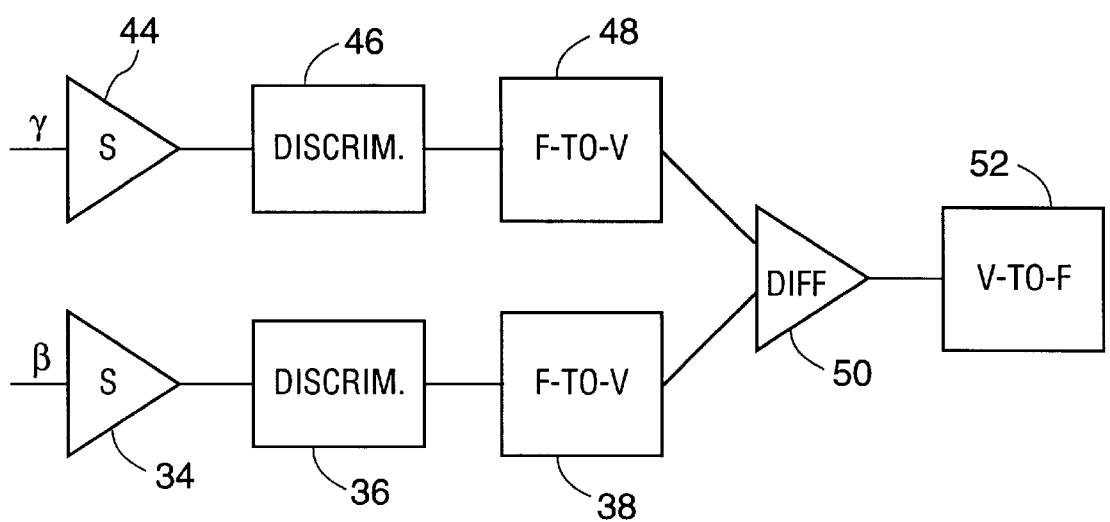
FIG. 9 provides a schematic illustration of a dual-detector probe utilizing the dual detector system as illustrated in FIG. 8.

FIGS. 8 and 9 illustrate an alternative and preferred embodiment of the beta probe of the present invention. In this design, a pair of semiconductor detectors 30 and 40 are "stacked" one behind the other in the tip of the probe 20, placed in a housing, 22, as shown in FIG. 8, with the front detector 30 serving as a beta shield for the rear detector 40. Although a pair of ion-implanted silicon detectors are utilized in a particularly preferred embodiment, it is contemplated that any matching pair of semiconductor-based detectors can be advantageously used in the dual-detector design of the present invention, including surface barrier detectors, since the dual detector design itself significantly reduces the effects of background photons and gamma rays.

As noted previously, it is contemplated that both detectors 30 and 40 can be biased using the same power supply, and that the resulting signal from each detector will be processed individually. Therefore, in the preferred embodiment each detector 30 and 40 has a separate preamplifier 32 and 42 for amplifying and shaping the electrical signal into an appropriate voltage pulse. As before, the preamplifiers 32 and 42 are ideally located as close to their respective detectors as possible, in order to reduce electrical noise. Referring now to FIG. 9, amplifiers 34 and 44 are coupled to the preamplifiers 32 and 42 for further amplifying the electrical signal, and in a particularly preferred embodiment discriminators 36 and 46 are coupled to the amplifiers 34 and 44 for further filtering of noise, and to help reduce the gamma ray component of the electrical signal, as discussed above.

In a preferred embodiment, the detectors are shielded. In such an embodiment, the shielding can comprise lead shielding or carbon fiber around the detectors except at their absorbance face (i.e., the surface of the detector intended to absorb radiation particles).

Figure 10:
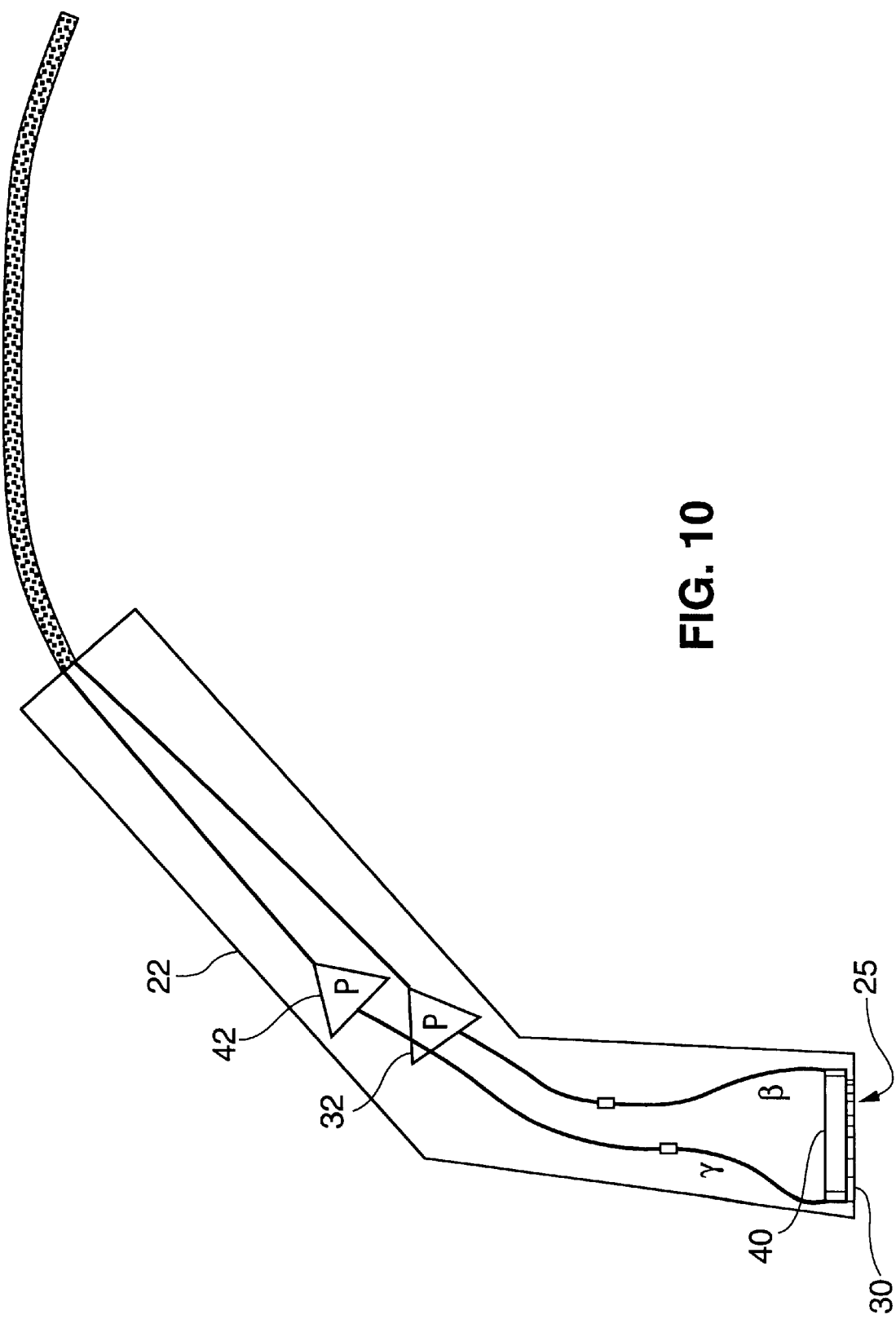
FIG. 10 illustrates another preferred embodiment of the device of present invention, utilizing two semiconductor-based detectors stacked in the tip of a probe and preamplifiers contained within the housing.

FIG. 10 provides an illustration of another embodiment of the present invention. It has the features as described for FIG. 8 with the exception that the preamplifiers, 32 and 42, are placed within the housing, 22. An entrance window, 25, is placed at the end of the housing, 22, defining the tip.

It is contemplated that signal subtraction can be accomplished either digitally, with a microprocessor, or in an analog fashion. In a preferred embodiment, the discriminated signals are converted (FIG. 9) to a voltage level using frequency-to-voltage converters 38 and 48 coupled to the respective discriminators 36 and 46, and the signal from the rear detector 40 is then subtracted from the signal from the front detector 30 using a difference amplifier 50. In a further embodiment, the resulting voltage level can be reconverted to a digital signal, if desired, by using a frequency-to-voltage converter 52. Thus, the gamma ray or photon component of the signal from the front detector will be substantially reduced or eliminated after subtraction of the signal from the rear detector, resulting in a more accurate reading of the beta emissions.

From the above it is clear that the present invention provides for a method and apparatus which can accurately detect beta-emitting radiopharmaceuticals accumulated within lesions in the body, while substantially reducing the effect of background gamma ray contamination. While preferred embodiments have been described in some detail, it should be apparent from the above discussion that many modifications and variations are possible without deviating from the invention. For example, while the examples provided herein described the preferential detection of beta emissions from $^{18}$F-FDG, similar results have been obtained by the present inventors for both $^{131}$I and $^{111}$In. Similarly, the substantial reduction in the size of the probe enabled by the present invention facilitates its application to endoscopy, bronchoscopy, colposcopy, colonoscopy, cystoscopy, laparoscopy and thorascopy, as well as other forms of minimally-invasive or non-invasive surgical biopsy. It is also contemplated that an array of detectors as described herein could be incorporated into a radiopharmaceutical probe and arranged to produce an image of the signal distribution. Furthermore, other improvements and modifications which become apparent to persons of ordinary skill in the art only after reading this disclosure, the drawings and the following claims are deemed within the spirit and scope of the present invention.

We claim:

1. A device, comprising:
    a) a housing, comprising a rear portion and a front portion, said front portion comprising an aluminum radiation entrance window defining a tip and the end of the front portion of said housing, said window permitting the transmission of gamma radiation and wherein the remainder of the housing blocks the transmission of gamma radiation;
    b) first and second radiation detectors disposed within said housing at said tip, said first detector capable of detecting beta particles and gamma radiation and serving to shield said second detector from at least a portion of the beta particles detected by said first detector.

2. The device of claim 1, wherein said first detector is positioned in front of said second detector in a manner such that gamma radiation reaching said tip of said device contacts said first detector prior to contacting said second detector.

3. The device of claim 2, wherein said first and second detectors are semiconductor detectors.

4. The device of claim 3, wherein said semiconductor detectors are ion-implanted silicon detectors.

5. The device of claim 3, wherein said semiconductor detectors are surface barrier detectors.

6. The device of claim 2, wherein said first and second detectors comprise circular silicon wafers of identical dimensions.

7. The device of claim 1, further comprising first and second preamplifiers contained within said housing, said first preamplifier coupled to said first detector and said second preamplifier coupled to said second detector.

8. The device of claim 7, wherein said preamplifiers are both connected to a power supply.

9. A device, comprising:
    a) an elongated housing, comprising a hand-graspable rear portion and a front portion, said front portion comprising a cylindrical tip; and
    b) first and second semiconductor detectors disposed within said housing at said tip, said first detector capable of detecting beta particles and gamma radiation and serving to shield said second detector from at least a portion of the beta particles detected by said first detector.

10. The device of claim 9, further comprising a radiation entrance window defining said tip and the end of the front portion of said housing.

11. The device of claim 10, wherein said first detector is positioned in front of said second detector relative to said radiation entrance window in a manner such that radiation reaching said tip of said device contacts said first detector prior to contacting said second detector.

12. The device of claim 9, wherein said semiconductor detectors are ion-implanted silicon detectors.

13. The device of claim 9, wherein said semiconductor detectors are surface barrier detectors.

14. The device of claim 9, wherein said first and second detectors comprise circular silicon wafers of identical dimensions.

15. The device of claim 9, further comprising first and second preamplifiers contained within said housing, said first preamplifier coupled to said first detector and said second preamplifier coupled to said second detector.

16. The device of claim 15, wherein said preamplifiers are both connected to a power supply.

17. A device, comprising:
    a) an elongated housing, comprising a hand-graspable rear portion and a front portion, said front portion comprising a cylindrical tip having a radiation entrance window, wherein said radiation entrance window permits the transmission of gamma radiation and wherein the remainder of the housing blocks the transmission of gamma radiation; and b) first and second semiconductor radiation detectors disposed within said housing at said tip, wherein said first detector is positioned in front of said second detector relative to said radiation entrance window in a manner such that radiation reaching said tip of said device contacts said first detector prior to contacting said second detector, said first detector capable of detecting beta particles and gamma radiation and serving to shield said second detector from at least a portion of the beta particles detected by said first detector.

18. The device of claim 17, wherein said semiconductor radiation detectors are ion-implanted silicon detectors.

19. The device of claim 17, wherein said semiconductor radiation detectors are surface barrier detectors.

20. The device of claim 17, wherein said first and second detectors comprise circular silicon wafers of identical dimensions.

21. The device of claim 17, further comprising first and second preamplifiers contained within said housing, said first preamplifier coupled to said first detector and said second preamplifier coupled to said second detector.

22. The device of claim 21, wherein said preamplifiers are both connected to a power supply.

23. A probe system for detecting radiation emitted from a radiopharmaceutical in a diseased tissue, comprising:

a) a probe having first and second radiation detectors said first radiation detector generates an electrical signal in response to the passage of radiation into said first detector from a radiopharmaceutical in diseased tissue, said first detector capable of detecting beta particles and gamma radiation while serving to shield said second detector from at least a portion of the beta particles detected by said first detector; and b) an optical transmitter coupled to said probe for transmitting said electrical signal as an optical signal to a remote location.

* * * * *